US005552524A

United States Patent [19]

Basinski et al.

[11] Patent Number: 5,552,524

[45] Date of Patent: Sep. 3, 1996

[54] ANTI-OBESITY PROTEINS

[75] Inventors: Margret B. Basinski, Indianapolis; Richard D. DiMarchi, Carmel; William F. Heath, Jr., Fishers; Brigitte E. Schoner, Monrovia, all of Ind.

[73] Assignee: Eli Lilly and Company, Indianapolis, Ind.

[21] Appl. No.: 384,292

[22] Filed: Feb. 6, 1995

Related U.S. Application Data

[63] Continuation-in-part of Ser. No. 381,661, Jan. 31, 1995, abandoned.

[51] Int. Cl.$^6$ ............................ A61K 38/00; C07K 7/00; C07K 7/10

[52] U.S. Cl. ............................................ 530/324; 530/350

[58] Field of Search .................................... 530/324, 350; 514/12

[56] References Cited

U.S. PATENT DOCUMENTS 4,626,549 12/1986 Molloy et al. .......................... 514/651

5,304,493 4/1994 Nowak ...................................... 436/56

OTHER PUBLICATIONS

Chem. Abstract 94–304407/38, Nagata Sangyo Co. Ltd. (Mar. 29, 1993).

Zhang, et al., "Positional cloning of the mouse obese gene and its human homologue", *Nature*, 372:1, 425–432 (Dec. 1, 1994).

Rink, "In search of a satiety factor", *Nature*, 372:1, 406–407 (Dec. 1, 1994).

Flam, "Obesity Gene Discovery May Help Solve Weighty Problem", *Science*, 266, 1477–1478 (Dec. 2, 1994).

Marx, "Obesity Gene Discovery May Help Solve Weighty Problem", Science, 266, 1477–1478 (Dec. 2, 1994).

*Primary Examiner*—Elizabeth C. Weimar
*Assistant Examiner*—S. G. Marshall
*Attorney, Agent, or Firm*—Steven P. Caltrider; David E. Boone

[57] ABSTRACT

The present invention provides anti-obesity proteins, which when administered to a patient regulate fat tissue. Accordingly, such agents allow patients to overcome their obesity handicap and live normal lives with much reduced risk for type II diabetes, cardiovascular disease and cancer.

15 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 138 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 4
( D ) OTHER INFORMATION: /note="Xaa at position 4 of SEQ ID NO: 1 is Gln or Glu;"

( i x ) FEATURE:
( A ) NAME/KEY: Modified-site
( B ) LOCATION: 7
( D ) OTHER INFORMATION: /note="Xaa at position 7 of SEQ ID NO: 1 is Gln or Glu;"

( i x ) FEATURE:
( A ) NAME/KEY: Modified-site
( B ) LOCATION: 22
( D ) OTHER INFORMATION: /note="Xaa at position 22 of SEQ ID NO: 1 is Asn, Asp or Gln;"

( i x ) FEATURE:
( A ) NAME/KEY: Modified-site
( B ) LOCATION: 27
( D ) OTHER INFORMATION: /note="Xaa at position 27 of SEQ ID NO: 1 is Thr or Ala;"

( i x ) FEATURE:
( A ) NAME/KEY: Modified-site
( B ) LOCATION: 28
( D ) OTHER INFORMATION: /note="Xaa at position 28 of SEQ ID NO: 1 is Gln, Glu or absent;"

( i x ) FEATURE:
( A ) NAME/KEY: Modified-site
( B ) LOCATION: 34
( D ) OTHER INFORMATION: /note="Xaa at position 34 of SEQ ID NO: 1 is Gln or Glu;"

( i x ) FEATURE:
( A ) NAME/KEY: Modified-site
( B ) LOCATION: 54
( D ) OTHER INFORMATION: /note="Xaa at position 54 of SEQ ID NO: 1 is Met, methionine sulfoxide, Leu, Ile, Val, Ala, or Gly;"

( i x ) FEATURE:
( A ) NAME/KEY: Modified-site
( B ) LOCATION: 56
( D ) OTHER INFORMATION: /note="Xaa at position 56 of SEQ ID NO: 1 is Gln or Glu;"

( i x ) FEATURE:
( A ) NAME/KEY: Modified-site
( B ) LOCATION: 62
( D ) OTHER INFORMATION: /note="Xaa at position 62 of SEQ ID NO: 1 is Gln or Glu;"

( i x ) FEATURE:
( A ) NAME/KEY: Modified-site
( B ) LOCATION: 63
( D ) OTHER INFORMATION: /note="Xaa at position 63 of SEQ ID NO: 1 is Gln or Glu;"

( i x ) FEATURE:
( A ) NAME/KEY: Modified-site
( B ) LOCATION: 68
( D ) OTHER INFORMATION: /note="Xaa at position 68 of SEQ ID NO: 1 is Met, methionine sulfoxide, Leu, Ile, Val, Ala, or Gly;"

( i x ) FEATURE:
( A ) NAME/KEY: Modified-site
( B ) LOCATION: 72
( D ) OTHER INFORMATION: /note="Xaa at position 72 of SEQ ID NO: 1 is Asn, Asp or Gln;"

( i x ) FEATURE:
( A ) NAME/KEY: Modified-site
( B ) LOCATION: 75
( D ) OTHER INFORMATION: /note="Xaa at position 75 of SEQ ID NO: 1 is Gln or Glu;"

( i x ) FEATURE:
( A ) NAME/KEY: Modified-site
( B ) LOCATION: 78
( D ) OTHER INFORMATION: /note="Xaa at position 78 of SEQ ID NO: 1 is Asn, Asp or Gln;"

( i x ) FEATURE:
( A ) NAME/KEY: Modified-site
( B ) LOCATION: 82
( D ) OTHER INFORMATION: /note="Xaa at position 82 of SEQ ID NO: is Asn, Asp or Gln;"

( i x ) FEATURE:
( A ) NAME/KEY: Modified-site
( B ) LOCATION: 100
( D ) OTHER INFORMATION: /note="Xaa at position 100 of SEQ ID NO: 1 is Gln, Trp, Tyr, Phe, Ile, Val, or Leu;"

( i x ) FEATURE:
( A ) NAME/KEY: Modified-site
( B ) LOCATION: 130
( D ) OTHER INFORMATION: /note="Xaa at position 130 of SEQ ID NO: 1 is Gln or Glu;"

( i x ) FEATURE:
( A ) NAME/KEY: Modified-site
( B ) LOCATION: 134
( D ) OTHER INFORMATION: /note="Xaa at position 134 of SEQ ID NO: 1 is Gln or Glu;"

( i x ) FEATURE:
( A ) NAME/KEY: Modified-site
( B ) LOCATION: 136
( D ) OTHER INFORMATION: /note="Xaa at position 136 of SEQ ID NO: 1 is Met, methionine sulfoxide, Leu, Ile, Val, Ala, or Gly;"

( i x ) FEATURE:
( A ) NAME/KEY: Modified-site
( B ) LOCATION: 138
( D ) OTHER INFORMATION: /note="Xaa at position 138 of SEQ ID NO: 1 is Trp or Gln;"

( x i ) SEQUENCE DESCRIPTION: SEQ ID NO:1:

| | | | | | | | | | | | | | | | |
|---|---|---|---|---|---|---|---|---|---|---|---|---|---|---|---|
| Val | Pro | Ile | Xaa | Lys | Val | Xaa | Asp | Asp | Thr | Lys | Thr | Leu | Ile | Lys | Thr |
| 1 | | | | 5 | | | | | 10 | | | | | 15 | |
| Ile | Val | Thr | Arg | Ile | Xaa | Asp | Ile | Ser | His | Xaa | Xaa | Ser | Val | Ser | Ser |
| | | | 20 | | | | | 25 | | | | | 30 | | |
| Lys | Xaa | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Xaa | Asp | Xaa | Thr | Leu | Ala | Val | Tyr | Xaa | Xaa | Ile |
| | 50 | | | | | 55 | | | | | 60 | | | | |
| Leu | Thr | Ser | Xaa | Pro | Ser | Arg | Xaa | Val | Ile | Xaa | Ile | Ser | Xaa | Asp | Leu |
| 65 | | | | | 70 | | | | | 75 | | | | | 80 |
| Glu | Xaa | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Xaa | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | 115 | | | | | 120 | | | | | 125 | | | |
| Leu | Xaa | Gly | Ser | Leu | Xaa | Asp | Xaa | Leu | Xaa | | | | | | |
| | 130 | | | | | 135 | | | | | | | | | |

( 2 ) INFORMATION FOR SEQ ID NO:2:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="Xaa at position 1 of SEQ ID NO: 2 is Gln or Glu."

( x i ) SEQUENCE DESCRIPTION: SEQ ID NO:2:

-continued

```
Xaa Leu Asp Leu Ser Pro Gly Cys
1               5
```

( 2 ) INFORMATION FOR SEQ ID NO:3:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

```
GGGGCATATG AGGGTACCTA TCCAGAAAGT CCAGGATGAC AC          42
```

( 2 ) INFORMATION FOR SEQ ID NO:4:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

```
GGGGGGATCC TATTAGCACC CGGGAGACAG GTCCAGCTGC CACAACAT          48
```

ANTI-OBESITY PROTEINS

This application is a continuation-in-part of DiMarchi et al., U.S. Ser. No. 08/381,661, filed Jan. 31, 1995, docket number X-9947 now abandoned.

FIELD OF THE INVENTION

The present invention is in the field of human medicine, particularly in the treatment of obesity and disorders associated with obesity. Most specifically the invention relates to anti-obesity proteins that when administered to a patient regulate fat tissue.

BACKGROUND OF THE INVENTION

Obesity, and especially upper body obesity, is a common and very serious public health problem in the United States and throughout the world. According to recent statistics, more than 25% of the United States population and 27% of the Canadian population are over weight. Kuczmarski, *Amer. J. of Clin. Nut.* 52: 495S–502S (1992); Reeder et. al., *Can. Med. Ass. J.*, 23:226–233 (1992). Upper body obesity is the strongest risk factor known for type II diabetes mellitus, and is a strong risk factor for cardiovascular disease and cancer as well. Recent estimates for the medical cost of obesity are $150,000,000,000 world wide. The problem has become serious enough that the surgeon general has begun an initiative to combat the ever increasing adiposity rampant in American society.

Much of this obesity induced pathology can be attributed to the strong association with dyslipidemia, hypertension, and insulin resistance. Many studies have demonstrated that reduction in obesity by diet and exercise reduces these risk factors dramatically. Unfortunately these treatments are largely unsuccessful with a failure rate reaching 95%. This failure may be due to the fact that the condition is strongly associated with genetically inherited factors that contribute to increased appetite, preference for highly caloric foods, reduced physical activity, and increased lipogenic metabolism. This indicates that people inheriting these genetic traits are prone to becoming obese regardless of their efforts to combat the condition. Therefore, a new pharmacological agent that can correct this adiposity handicap and allow the physician to successfully treat obese patients in spite of their genetic inheritance is needed.

The ob/ob mouse is a model of obesity and diabetes that is known to carry an autosomal recessive trait linked to a mutation in the sixth chromosome. Recently, Yiying Zhang and co-workers published the positional cloning of the mouse gene linked with this condition. Yiying Zhang et al. *Nature* 372:425–32 (1994). This report disclosed a gene coding for a 167 amino acid protein with a 21 amino acid signal peptide that is exclusively expressed in adipose tissue. The report continues to disclose that a mutation resulting in the conversion of a codon for arginine at position 105 to a stop codon results in the expression of a truncated protein, which presumably is inactive.

Physiologist have postulated for years that, when a mammal overeats, the resulting excess fat signals to the brain that the body is obese which, in turn, causes the body to eat less and burn more fuel. G. R. Hervey, *Nature* 227:629–631 (1969). This "feedback" model is supported by parabiotic experiments, which implicate a circulating hormone controlling adiposity. Based on this model, the protein, which is apparently encoded by the ob gene, is now speculated to be an adiposity regulating hormone.

Pharmacological agents which are biologically active and mimic the activity of this protein are useful to help patients regulate their appetite and metabolism and thereby control their adiposity. Until the present invention, such a pharmacological agent was unknown.

The present invention provides biologically active anti-obesity proteins. Such agents therefore allow patients to overcome their obesity handicap and live normal lives with a more normalized risk for type II diabetes, cardiovascular disease and cancer.

SUMMARY OF INVENTION

The present invention is directed to a biologically active anti-obesity protein of the Formula (I):

SEQ ID NO: 1

| | | | | | | | | | | | | | | |
|---|---|---|---|---|---|---|---|---|---|---|---|---|---|---|
| 1 | | | | 5 | | | | | 10 | | | | | 15 |
| Val | Pro | Ile | Xaa | Lys | Val | Xaa | Asp | Asp | Thr | Lys | Thr | Leu | Ile | Lys |
| | | | | 20 | | | | | 25 | | | | | 30 |
| Thr | Ile | Val | Thr | Arg | Ile | Xaa | Asp | Ile | Ser | His | Xaa | Xaa | Ser | Val |
| | | | | 35 | | | | | 40 | | | | | 45 |
| Ser | Ser | Lys | Xaa | Lys | Val | Thr | Gly | Leu | Asp | Phe | Ile | Pro | Gly | Leu |
| | | | | 50 | | | | | 55 | | | | | 60 |
| His | Pro | Ile | Leu | Thr | Leu | Ser | Lys | Xaa | Asp | Xaa | Thr | Leu | Ala | Val |
| | | | | 65 | | | | | 70 | | | | | 75 |
| Tyr | Xaa | Xaa | Ile | Leu | Thr | Ser | Xaa | Pro | Ser | Arg | Xaa | Val | Ile | Xaa |
| | | | | 80 | | | | | 85 | | | | | 90 |
| Ile | Ser | Xaa | Asp | Leu | Glu | Xaa | Leu | Arg | Asp | Leu | Leu | His | Val | Leu |

-continued

| | | | | | | | | | | | | | | | |
|---|---|---|---|---|---|---|---|---|---|---|---|---|---|---|---|
| | | | | | 95 | | | | | 100 | | | | | 105 |
| | Ala | Phe | Ser | Lys | Ser | Cys | His | Leu | Pro | Xaa | Ala | Ser | Gly | Leu | Glu |
| S | | | | | | | | | | | | | | | |
| | | | | | 110 | | | | | 115 | | | | | 120 |
| | Thr | Leu | Asp | Ser | Leu | Gly | Gly | Val | Leu | Glu | Ala | Ser | Gly | Tyr | Ser |
| | | | | | 125 | | | | | 130 | | | | | 135 |
| | Thr | Glu | Val | Val | Ala | Leu | Ser | Arg | Leu | Xaa | Gly | Ser | Leu | Xaa | Asp |
| | Xaa | Leu | Xaa | | | | | | | | | | | | |

SEQ ID NO: 2

| | | | | | | | | | |
|---|---|---|---|---|---|---|---|---|---|
| | 1 | | | | 5 | | | | |
| | Xaa | Leu | Asp | Leu | Ser | Pro | Gly | Cys | |
| S | | | | | | | | | |

wherein:

Xaa at position 4 of SEQ ID NO: 1 is Gln or Glu;

Xaa at position 7 of SEQ ID NO: 1 is Gln or Glu;

Xaa at position 22 of SEQ ID NO: 1 is Asn, Asp or Gln;

Xaa at position 27 of SEQ ID NO: 1 is Thr or Ala;

Xaa at position 28 of SEQ ID NO: 1 is Gin, Glu or absent;

Xaa at position 34 of SEQ ID NO: 1 is Gln or Glu;

Xaa at position 54 of SEQ ID NO: 1 is Met, methionine sulfoxide, Leu, Ile, Val, Ala, or Gly;

Xaa at position 56 of SEQ ID NO: 1 is Gln or Glu;

Xaa at position 62 of SEQ ID NO: 1 is Gln or Glu;

Xaa at position 63 of SEQ ID NO: 1 is Gln or Glu;

Xaa at position 68 of SEQ ID NO: 1 is Met, methionine sulfoxide, Leu, Ile, Val, Ala, or Gly;

Xaa at position 72 of SEQ ID NO: 1 is Asn, Asp or Gln;

Xaa at position 75 of SEQ ID NO: 1 is Gln or Glu;

Xaa at position 78 of SEQ ID NO: 1 is Asn, Asp or Gln;

Xaa at position 82 of SEQ ID NO: 1 is Ash, Asp or Gln;

Xaa at position 100 of SEQ ID NO: 1 is Gln, Trp, Tyr, Phe, Ile, Val, or Leu;

Xaa at position 130 of SEQ ID NO: 1 is Gln or Glu;

Xaa at position 134 of SEQ ID NO: 1 is Gln or Glu;

Xaa at position 136 of SEQ ID NO: 1 is Met, methionine sulfoxide, Leu, Ile, Val, Ala, or Gly;

Xaa at position 138 of SEQ ID NO: 1 is Trp or Gln; and

Xaa at position 1 of SEQ ID NO: 2 is Gln or Glu.

The invention further provides a method of treating obesity, which comprises administering to a mammal in need thereof a protein of the Formula (I).

The invention further provides a pharmaceutical formulation, which comprises a protein of the Formula (I) together with one or more pharmaceutical acceptable diluents, carriers or excipients therefor.

DETAILED DESCRIPTION

As noted above the present invention provides a protein of the Formula (I):

SEQ ID NO: 1

| | | | | | | | | | | | | | | |
|---|---|---|---|---|---|---|---|---|---|---|---|---|---|---|
| 1 | | | | 5 | | | | | 10 | | | | | 15 |
| Val | Pro | Ile | Xaa | Lys | Val | Xaa | Asp | Asp | Thr | Lys | Thr | Leu | Ile | Lys |
| | | | | 20 | | | | | 25 | | | | | 30 |
| Thr | Ile | Val | Thr | Arg | Ile | Xaa | Asp | Ile | Ser | His | Xaa | Xaa | Ser | Val |
| | | | | 35 | | | | | 40 | | | | | 45 |
| Ser | Ser | Lys | Xaa | Lys | Val | Thr | Gly | Leu | Asp | Phe | Ile | Pro | Gly | Leu |
| | | | | 50 | | | | | 55 | | | | | 60 |
| His | Pro | Ile | Leu | Thr | Leu | Ser | Lys | Xaa | Asp | Xaa | Thr | Leu | Ala | Val |
| | | | | 65 | | | | | 70 | | | | | 75 |
| Tyr | Xaa | Xaa | Ile | Leu | Thr | Ser | Xaa | Pro | Ser | Arg | Xaa | Val | Ile | Xaa |
| | | | | 80 | | | | | 85 | | | | | 90 |
| Ile | Ser | Xaa | Asp | Leu | Glu | Xaa | Leu | Arg | Asp | Leu | Leu | His | Val | Leu |

-continued

```
                    95                    100                   105
    Ala  Phe  Ser  Lys  Ser  Cys  His  Leu  Pro  Xaa  Ala  Ser  Gly  Leu  Glu
S                         |
                    110                   115                   120
    Thr  Leu  Asp  Ser  Leu  Gly  Gly  Val  Leu  Glu  Ala  Ser  Gly  Tyr  Ser

                    125                   130                   135
    Thr  Glu  Val  Val  Ala  Leu  Ser  Arg  Leu  Xaa  Gly  Ser  Leu  Xaa  Asp

    Xaa  Leu  Xaa

                                   SEQ ID NO: 2

    1                   5
    Xaa  Leu  Asp  Leu  Ser  Pro  Gly  Cys
S                                         |
```

wherein:

Xaa at position 4 of SEQ ID NO: 1 is Gln or Glu;
Xaa at position 7 of SEQ ID NO: 1 is Gln or Glu;
Xaa at position 22 of SEQ ID NO: 1 is Asn, Asp or Gln;
Xaa at position 27 of SEQ ID NO: 1 is Thr or Ala;
Xaa at position 28 of SEQ ID NO: 1 is Gln, Glu or absent;
Xaa at position 34 of SEQ ID NO: 1 is Gln or Glu;
Xaa at position 54 of SEQ ID NO: 1 is Met, methionine sulfoxide, Leu, Ile, Val, Ala, or Gly;
Xaa at position 56 of SEQ ID NO: 1 is Gln or Glu;
Xaa at position 62 of SEQ ID NO: 1 is Gln or Glu;
Xaa at position 63 of SEQ ID NO: 1 is Gln or Glu;
Xaa at position 68 of SEQ ID NO: 1 is Met, methionine sulfoxide, Leu, Ile, Val, Ala, or Gly;
Xaa at position 72 of SEQ ID NO: 1 is Asn, Asp or Gln;
Xaa at position 75 of SEQ ID NO: 1 is Gln or Glu;
Xaa at position 78 of SEQ ID NO: 1 is Asn, Asp or Gln;
Xaa at position 82 of SEQ ID NO: 1 is Asn, Asp or Gln;
Xaa at position 100 of SEQ ID NO: 1 is Gln, Trp, Tyr, Phe, Ile, Val, or Leu;
Xaa at position 130 of SEQ ID NO: 1 is Gln or Glu;
Xaa at position 134 of SEQ ID NO: 1 is Gln or Glu;
Xaa at position 136 of SEQ ID NO: 1 is Met, methionine sulfoxide, Leu, Ile, Val, Ala, or Gly;
Xaa at position 138 of SEQ ID NO: 1 is Trp or Gln; and
Xaa at position 1 of SEQ ID NO: 2 is Gln or Glu.

The preferred proteins of the present invention are those of Formula (I) wherein:
wherein:

Xaa at position 4 of SEQ ID NO: 1 is Gln;
Xaa at position 7 of SEQ ID NO: 1 is Gln;
Xaa at position 22 of SEQ ID NO: 1 is Asn;
Xaa at position 27 of SEQ ID NO: 1 is Thr;
Xaa at position 28 of SEQ ID NO: 1 is Gln;
Xaa at position 34 of SEQ ID NO: 1 is Gln;
Xaa at position 54 of SEQ ID NO: 1 is Met;
Xaa at position 56 of SEQ ID NO: 1 is Gln;
Xaa at position 62 of SEQ ID NO: 1 is Gln;
Xaa at position 63 of SEQ ID NO: 1 is Gln;
Xaa at position 68 of SEQ ID NO: 1 is Met;
Xaa at position 72 of SEQ ID NO: 1 is Asn;
Xaa at position 75 of SEQ ID NO: 1 is Gln;
Xaa at position 78 of SEQ ID NO: 1 is Asn;
Xaa at position 82 of SEQ ID NO: 1 is Asn;
Xaa at position 100 of SEQ ID NO: 1 is Trp;
Xaa at position 130 of SEQ ID NO: 1 is Gln;
Xaa at position 134 of SEQ ID NO: 1 is Gln;
Xaa at position 136 of SEQ ID NO: 1 is Met;
Xaa at position 138 of SEQ ID NO: 1 is Trp; and
Xaa at position 1 of SEQ ID NO: 2 is Gln.

The amino acids abbreviations are accepted by the United States Patent and Trademark Office as set forth in 37 C.F.R. § 1.822 (b)(2) (1993). One skilled in the art would recognize that certain amino acids are prone to rearrangement. For example, Asp may rearrange to aspartimide and isoaspartigine as described in I. Schön et al., *Int. J. Peptide Protein Res.* 14:485–94 (1979) and references cited therein. These rearrangement derivatives are included within the scope of the present invention. Unless otherwise indicated the amino acids are in the L configuration.

For purposes of the present invention, as disclosed and claimed herein, the following terms and abbreviations are defined as follows:

SEQ ID NO:1 properly crosslinked to SEQ ID NO: 2 refers to the formation of a disulfide bond between cysteine residues at position 96 of SEQ ID NO: 1 and position 8 of SEQ ID NO: 2 as depicted in Formula I.

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

Chelating Peptide—An amino acid sequence capable of complexing with a multivalent metal ion.

DNA—Deoyxribonucleic acid.

EDTA—an abbreviation for ethylenediamine tetraacetic acid.

$ED_{50}$—an abbreviation for half-maximal value.

FAB-MS—an abbreviation for fast atom bombardment mass spectrometry.

Immunoreactive Protein(s)—a term used to collectively describe antibodies, fragments of antibodies capable of binding antigens of a similar nature as the parent antibody molecule from which they are derived, and single chain polypeptide binding molecules as described in PCT Application No. PCT/US 87/02208, International Publication No. WO 88/01649.

mRNA—messenger RNA.

MWCO—an abbreviation for molecular weight cut-off.

Plasmid—an extrachromosomal self-replicating genetic element.

PMSF—an abbreviation for phenylmethylsulfonyl fluoride.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Tris—an abbreviation for tris(hydroxymethyl)aminomethane.

Treating—describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating obesity therefor includes the inhibition of food intake, the inhibition of weight gain, and inducing weight loss in patients in need thereof.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. Vectors include Recombinant DNA cloning vectors and Recombinant DNA expression vectors.

X-gal—an abbreviation for 5-bromo-4-chloro-3-idolyl beta-D-galactoside.

SEQ ID NO: 1 refers to the sequence set forth in the sequence listing and means an anti-obesity protein of the formula:

SEQ ID NO: 1

| | | | | | | | | | | | | | | |
|---|---|---|---|---|---|---|---|---|---|---|---|---|---|---|
| 1 | | | | 5 | | | | | 10 | | | | | 15 |
| Val | Pro | Ile | Xaa | Lys | Val | Xaa | Asp | Asp | Thr | Lys | Thr | Leu | Ile | Lys |
| | | | | 20 | | | | | 25 | | | | | 30 |
| Thr | Ile | Val | Thr | Arg | Ile | Xaa | Asp | Ile | Ser | His | Xaa | Xaa | Ser | Val |
| | | | | 35 | | | | | 40 | | | | | 45 |
| Ser | Ser | Lys | Xaa | Lys | Val | Thr | Gly | Leu | Asp | Phe | Ile | Pro | Gly | Leu |
| | | | | 50 | | | | | 55 | | | | | 60 |
| His | Pro | Ile | Leu | Thr | Leu | Ser | Lys | Xaa | Asp | Xaa | Thr | Leu | Ala | Val |
| | | | | 65 | | | | | 70 | | | | | 75 |
| Tyr | Xaa | Xaa | Ile | Leu | Thr | Ser | Xaa | Pro | Ser | Arg | Xaa | Val | Ile | Xaa |
| | | | | 80 | | | | | 85 | | | | | 90 |
| Ile | Ser | Xaa | Asp | Leu | Glu | Xaa | Leu | Arg | Asp | Leu | Leu | His | Val | Leu |
| | | | | 95 | | | | | 100 | | | | | 105 |
| Ala | Phe | Ser | Lys | Ser | Cys | His | Leu | Pro | Xaa | Ala | Ser | Gly | Leu | Glu |
| | | | | 110 | | | | | 115 | | | | | 120 |
| Thr | Leu | Asp | Ser | Leu | Gly | Gly | Val | Leu | Glu | Ala | Ser | Gly | Tyr | Ser |
| | | | | 125 | | | | | 130 | | | | | 135 |
| Thr | Glu | Val | Val | Ala | Leu | Ser | Arg | Leu | Xaa | Gly | Ser | Leu | Xaa | Asp |
| Xaa | Leu | Xaa | | | | | | | | | | | | |

Replicon—A DNA sequence that controls and allows for autonomous replication of a plasmid or other vector.

RNA—ribonucleic acid.

RP-HPLC—an abbreviation for reversed-phase high performance liquid chromatography.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

wherein:

Xaa at position 4 of SEQ ID NO: 1 is Gln or Glu;

Xaa at position 7 of SEQ ID NO: 1 is Gln or Glu;

Xaa at position 22 of SEQ ID NO: 1 is Asn, Asp or Gln;

Xaa at position 27 of SEQ ID NO: 1 is Thr or Ala;

Xaa at position 28 of SEQ ID NO: 1 is Gln, Glu or absent;

Xaa at position 34 of SEQ ID NO: 1 is Gln or Glu;

Xaa at position 54 of SEQ ID NO: 1 is Met, methionine sulfoxide, Leu, Ile, Val, Ala, or Gly;

Xaa at position 56 of SEQ ID NO: 1 is Gln or Glu;

Xaa at position 62 of SEQ ID NO: 1 is Gln or Glu;

Xaa at position 63 of SEQ ID NO: 1 is Gln or Glu;

Xaa at position 68 of SEQ ID NO: 1 is Met, methionine sulfoxide, Leu, Ile, Val, Ala, or Gly;

Xaa at position 72 of SEQ ID NO: 1 is Asn, Asp or Gln;

Xaa at position 75 of SEQ ID NO: 1 is Gln or Glu;

Xaa at position 78 of SEQ ID NO: 1 is Ash, Asp or Gln;

Xaa at position 82 of SEQ ID NO: 1 is Asn, Asp or Gln;

Xaa at position 100 of SEQ ID NO: 1 is Gln, Trp, Tyr, Phe, Ile, Val, or Leu;

Xaa at position 130 of SEQ ID NO: 1 is Gln or Glu;

Xaa at position 134 of SEQ ID NO: 1 is Gln or Glu;

Xaa at position 136 of SEQ ID NO: 1 is Met, methionine sulfoxide, Leu, Ile, Val, Ala, or Gly; and Xaa at position 138 of SEQ ID NO: 1 is Trp or Gln.

SEQ ID NO: 2 refers to the sequence set forth in the sequence listing and means an anti-obesity protein of the formula:

SEQ ID NO: 2

```
1                   5
Xaa Leu Asp Leu Ser Pro Gly Cys
```

wherein:

Xaa at position 1 of SEQ ID NO: 2 is Gln or Glu.

Yiying Zhang et al. in *Nature* 372:425–32 (December 1994) report the cloning of the murine obese (ob) mouse gene and present mouse DNA and the naturally occurring amino acid sequence of the obesity protein for the mouse and human. This protein is speculated to be a hormone that is secreted by fat cells and controls body weight.

The present invention provides biologically active proteins that provide effective treatment for obesity. Many of the claimed proteins offer additional advantages of better absorption characteristics allowing administration nasally, bronchally, transdermally, or parentally. In addition, the claimed proteins improve in vivo stability or increased biological half-life.

The claimed proteins ordinarily are prepared by modification of the DNA encoding the claimed protein and thereafter expressing the DNA in recombinant cell culture. Techniques for making substitutional mutations at predetermined sites in DNA having a known sequence are well known, for example M13 primer mutagenesis. The mutations that might be made in the DNA encoding the present anti-obesity proteins must not place the sequence out of reading frame and preferably will not create complementary regions that could produce secondary mRNA structure. See DeBoer et al., EP 75,444A (1983).

The compounds of the present invention may be produced either by recombinant DNA technology or well known chemical procedures, such as solution or solid-phase peptide synthesis, or semi-synthesis in solution beginning with protein fragments coupled through conventional solution methods.

A. Solid Phase

The synthesis of the claimed protein may proceed by solid phase peptide synthesis or by recombinant methods. The principles of solid phase chemical synthesis of polypeptides are well known in the art and may be found in general texts in the area such as Dugas, H. and Penney, C., *Bioorganic Chemistry* Springer-Verlag, New York, pgs. 54–92 (1981). For example, peptides may be synthesized by solid-phase methodology utilizing an PE-Applied Biosystems 430A peptide synthesizer (commercially available from Applied Biosystems, Foster City Calif.) and synthesis cycles supplied by Applied Biosystems. Boc amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Arginine, Asparagine, Glutamine, Histidine and Methionine are coupled using preformed hydroxy benzotriazole esters. The following side chain protection may be used:

Arg, Tosyl

Asp, cyclohexyl or benzyl

Cys, 4-methylbenzyl

Glu, cyclohexyl

His, benzyloxymethyl

Lys, 2-chlorobenzyloxycarbonyl

Met, sulfoxide

Ser, Benzyl

Thr, Benzyl

Trp, formyl

Tyr, 4-bromo carbobenzoxy

Boc deprotection may be accomplished with trifluoroacetic acid (TFA) in methylene chloride. Formyl removal from Trp is accomplished by treatment of the peptidyl resin with 20% piperidine in dimethylformamide for 60 minutes at 4° C. Met(O) can be reduced by treatment of the peptidyl resin with TFA/dimethylsulfide/conHCl (95/5/1) at 25° C. for 60 minutes. Following the above pre-treatments, the peptides may be further deprotected and cleaved from the resin with anhydrous hydrogen fluoride containing a mixture of 10% m-cresol or m-cresol/10% p-thiocresol or m-cresol/p-thiocresol/dimethylsulfide. Cleavage of the side chain protecting group(s) and of the peptide from the resin is carried out at zero degrees Centigrade or below, preferably −20° C. for thirty minutes followed by thirty minutes at 0° C. After removal of the HF, the peptide/resin is washed with ether. The peptide is extracted with glacial acetic acid and lyophilized. Purification is accomplished by reverse-phase C18 chromatography (Vydac) column in 0.1% TFA with a gradient of increasing acetonitrile concentration.

One skilled in the art recognizes that the solid phase synthesis could also be accomplished using the FMOC strategy and a TFA/scavenger cleavage mixture.

B. Recombinant Synthesis

The claimed proteins may also be produced by recombinant methods. Recombinant methods are preferred if a high yield is desired. The basic steps in the recombinant production of protein include:

a) construction of a synthetic or semi-synthetic (or isolation from natural sources) DNA encoding the claimed protein, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

2.a. Gene Construction

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the claimed proteins. In the preferred practice of the invention, synthesis is achieved by recombinant DNA technology.

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic claimed protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may desirable in some applications to modify the coding sequence of the claimed protein so as to incorporate a convenient protease sensitive cleavage site, e.g., between the signal peptide and the structural protein facilitating the controlled excision of the signal peptide from the fusion protein construct.

The gene encoding the claimed protein may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual,* Cold Spring Harbor Press, Cold Spring Harbor Laboratory, Cold Spring Harbor, N.Y. (1989).

2.b. Direct Expression or Fusion Protein

The claimed protein may be made either by direct expression or as fusion protein comprising the claimed protein followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P., Site Specific Proteolysis of Fusion Proteins, Ch. 13 in *Protein Purification: From Molecular Mechanisms to Large Scale Processes,* American Chemical Soc., Washington, D.C. (1990).

2.c. Vector Construction

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. The claimed protein is a relatively large protein. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the claimed protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using DBR322, a plasmid derived from an *E. coli* species (Bolivar, et al., *Gene* 2:95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The genes encoding the protein of the present invention can be inserted into the plasmid backbone on a NdeI/BamHI restriction fragment cassette.

2.d. Procaryotic Expression

In general, procaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic, ATCC No. 27325), bacilli such as Bacillus subtilis, and other enterobacteriaceae such as Salmonella typhimurium or Serratia marcescans, and various pseudomonas species may be used. Promoters suitable for use with prokaryotic hosts include the β-lactamase (vector pGX2907 [ATCC 39344] contains the replicon and β-lactamase gene) and lactose promoter systems (Chang et al., *Nature,* 275:615 (1978); and Goeddel et al., *Nature* 281:544 (1979)), alkaline phosphatase, the tryptophan (trp) promoter system (vector pATHi [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

2.e. Eucaryotic Expression

The protein may be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature*, 273:113 (1978). The entire SV40 genome may be obtained from plasmid pBRSV, ATCC 45019. The immediate early promoter of the human cytomegalovirus may be obtained from plasmid pCMBD (ATCC 77177). Of course, promoters from the host cell or related species also are useful herein.

Transcription of a DNA encoding the claimed protein by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 5' (Laimins, L. et al., *PNAS* 78:993 (1981)) and 3' (Lusky, M. L., et al., *Mol. Cell Bio.* 3:1108 (1983)) to the transcription unit, within an intron (Banerji, J. L. et al., *Cell* 33:729 (1983)) as well as within the coding sequence itself (Osborne, T. F., et al., *Mol. Cell Bio.* 4:1293 (1984)). Many enhancer sequences are now known from mammalian genes (globin, RSV, SV40, EMC, elastase, albumin, afetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BglII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell's metabolism and the use of a mutant cell line which lacks the ability to grow without a supplemented media. Two examples are: CHO $DHFR^-$ cells (ATCC CRL-9096) and mouse $LTK^-$ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.* 1:327 (1982), mycophenolic acid, Mulligan, R. C. and Berg, P. *Science* 209:1422 (1980), or hygromycin, Sugden, B. et al., *Mol Cell. Biol.* 5:410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH5a (ATCC 31446) and successful transformants selected by antibiotic resistance where appropriate. Plasmids from the transformants are prepared, analyzed by restriction and/or sequence by the method of Messing, et al., *Nucleic Acids Res.* 4:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual,* Cold Spring Harbor Press, Cold Spring Harbor Laboratory, Cold Spring Harbor, N.Y. (1989), or *Current Protocols in Molecular Biology* (1989) and supplements.

Preferred suitable host cells for expressing the vectors encoding the claimed proteins in higher eukaryotes include: African green monkey kidney line cell line transformed by SV40 (COS-7, ATCC CRL-1651); transformed human primary embryonal kidney cell line 293, (Graham, F. L. et al., *J. Gen Virol.* 36:59–72 (1977), *Virology* 77:319–329, *Virology* 86:10–21); baby hamster kidney cells (BHK-21(C-13), ATCC CCL-10, *Virology* 16:147 (1962)); chinese hamster ovary cells CHO-$DHFR^-$ (ATCC CRL-9096), mouse Sertoli cells (TM4, ATCC CRL-1715, *Biol. Reprod.* 23:243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065);and mouse mammary tumor cells (MMT 060562, ATCC CCL51).

2.f. Yeast Expression

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (ATCC-40053, Stinchcomb, et al., *Nature* 282:39 (1979); Kingsman et al., *Gene* 7:141 (1979); Tschemper et al., *Gene* 10:157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85:12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 7090, 57091), zymomonas mobilis (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GAL1 found on plasmid pRY121 ATCC 37658) utilization. Suitable vectors and promoters for use in yeast expression are further described in R. Hitzeman et al., European Patent Publication No. 73,657A. Yeast enhancers such as the UAS Gal from Saccharomyces cerevisiae (found in conjunction with the CYC1 promoter on plasmid YEpsec—hI1beta ATCC 67024), also are advantageously used with yeast promoters.

The following examples are presented to further illustrate the preparation of the claimed proteins. The scope of the present invention is not to be construed as merely consisting of the following examples.

EXAMPLE 1

A DNA sequence encoding the following protein sequence:

–2
Met Arg - SEQ ID NO: 1.

is obtained using standard PCR methodology. A forward primer (5'-GG GG CAT ATG AGG GTA CCT ATC CAG AAA GTC CAG GAT GAC AC) SEQ ID NO:3 and a reverse primer (5'-GG GG GGATC CTA TTA GCA CCC GGG AGA CAG GTC CAG CTG CCA CAA CAT) SEQ ID NO:4 is used to amplify sequences from a human fat cell library (commercially available from CLONETECH). The PCR product is cloned into PCR-Script (available from STRATAGENE) and sequenced.

EXAMPLE 2

Vector Construction

A plasmid containing the DNA sequence encoding the desired claimed protein is constructed to include NdeI and BamHI restriction sites. The plasmid carrying the cloned PCR product is digested with NdeI and BamHI restriction enzymes. The small ~450 bp fragment is gel-purified and ligated into the vector pRB182 from which the coding sequence for A-C-B proinsulin is deleted. The ligation products are transformed into *E. coli* DH10B (commercially available from GIBCO-BRL) and colonies growing on tryptone-yeast (DIFCO) plates supplemented with 10 μg/mL of tetracycline are analyzed. Plasmid DNA is isolated, digested with NdeI and BamHI and the resulting fragments are separated by agarose gel electrophoresis. Plasmids containing the expected ~450 bp NdeI to BaSHI fragment are kept. *E. coli* B BL21 (DE3) (commercially available from NOVOGEN) are transformed with this second plasmid expression suitable for culture for protein production.

The techniques of transforming cells with the aforementioned vectors are well known in the art and may be found in such general references as Maniatis, et al. (1988) *Molecular Cloning: A Laboratory Manual,* Cold Spring Harbor Press, Cold Spring Harbor Laboratory, Cold Spring Harbor, N.Y. or *Current Protocols in Molecular Biology* (1989) and supplements. The techniques involved in the transformation of *E. coli* cells used in the preferred practice of the invention as exemplified herein are well known in the art. The precise conditions under which the transformed *E. coli* cells are cultured is dependent on the nature of the *E. coli* host cell line and the expression or cloning vectors employed. For example, vectors which incorporate thermoinducible promoter-operator regions, such as the c1857 thermoinducible lambda-phage promoter-operator region, require a temperature shift from about 30 to about 40 degrees C. in the culture conditions so as to induce protein synthesis.

In the preferred embodiment of the invention *E. coli* K12 RV308 cells are employed as host cells but numerous other cell lines are available such as, but not limited to, *E. coli* K12 L201, L687, L693, L507, L640, L641, L695, L814 (*E. coli* B). The transformed host cells are then plated on appropriate media under the selective pressure of the antibiotic corresponding to the resistance gene present on the expression plasmid. The cultures are then incubated for a time and temperature appropriate to the host cell line employed.

Proteins which are expressed in high-level bacterial expression systems characteristically aggregate in granules or inclusion bodies which contain high levels of the overexpressed protein. Kreuger et al., in *Protein Folding,* Gierasch and King, eds., pgs 136–142 (1990), American Association for the Advancement of Science Publication No. 89-18S, Washington, D.C. Such protein aggregates must be solubilized to provide further purification and isolation of the desired protein product. Id. A variety of techniques using strongly denaturing solutions such as guanidinium-HCl and/or weakly denaturing solutions such as dithiothreitol (DTT) are used to solubilize the proteins.

Gradual removal of the denaturing agents (often by dialysis) in a solution allows the denatured protein to assume its native conformation. The particular conditions for denaturation and folding are determined by the particular protein expression system and/or the protein in question.

Preferably, the present proteins are expressed as Met-Arg-SEQ ID NO: 1 so that the expressed proteins may be readily converted to the claimed protein with Cathepsin C. The purification of proteins is by techniques known in the art and includes reverse phase chromatography, affinity chromatography, and size exclusion.

The claimed proteins may exist, particularly when formulated, as dimers, trimers, tetramers, and other multimers. Such multimers are included within the scope of the present invention.

The present invention provides a method for treating obesity. The method comprises administering to the organism an effective amount of anti-obesity protein in a dose between about 1 and 1000 μg/kg. A preferred dose is from about 10 to 100 μg/kg of active compound. A typical daily dose for an adult human is from about 0.5 to 100 mg. In practicing this method, compounds of the Formula (I) can be administered in a single daily dose or in multiple doses per day. The treatment regime may require administration over extended periods of time. The amount per administered dose or the total amount administered will be determined by the physician and depend on such factors as the nature and severity of the disease, the age and general health of the patient and the tolerance of the patient to the compound.

The instant invention further provides pharmaceutical formulations comprising compounds of the Formula (I). The proteins, preferably in the form of a pharmaceutically acceptable salt, can be formulated for nasal, bronchal, transdermal, or parenteral administration for the therapeutic or prophylactic treatment of obesity. For example, compounds of the Formula (I) can be admixed with conventional pharmaceutical carriers and excipients. The compositions comprising claimed proteins contain from about 0.1 to 90% by weight of the active protein, preferably in a soluble form, and more generally from about 10 to 30%.

For intravenous (IV) use, the protein is administered in commonly used intravenous fluid(s) and administered by infusion. Such fluids, for example, physiological saline, Ringer's solution or 5% dextrose solution can be used.

For intramuscular preparations, a sterile formulation, preferably a suitable soluble salt form of a protein of the Formula (I), for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

It may also be desirable to administer the compounds of Formula (I) intranasally. Formulations useful in the intranasal absorption of proteins are well known in the art. Nasal formulations comprise the protein and carboxyvinyl polymer preferably selected from the group comprising the acrylic acid series hydrophilic crosslinked polymer, e.g. carbopole 934; 940, 941 (Goodrich Co.). The polymer accelerates absorption of the protein, and gives suitable viscosity to prevent discharge from nose. Suitable content of the polymer is 0.05–2 weight %. By neutralisation of the polymer with basic substance, thickening effect is increased. The amount of active compound is commonly 0.1–10%. The nasal preparation may be in drop form, spraying applicator or aerosol form.

The ability of the present compounds to treat obesity is demonstrated in vivo as follows:

Biological Testing for Anti-Obesity Proteins

Parabiotic experiments suggest that a protein is released by peripheral adipose tissue and that the protein is able to control body weight gain in normal, as well as obese mice. Therefore, the most closely related biological test is to inject the test article by any of several routes of administration (e.g. i.v., s.c., i.p., or by minipump or cannula) and then to monitor food and water consumption, body weight gain, plasma chemistry or hormones (glucose, insulin, ACTH, corticosterone, GH, T4) over various time periods.

Suitable test animals include normal mice (ICR, etc.) and obese mice (ob/ob, Avy/a, KK-Ay, tubby, fat). The mouse model of obesity and diabetes is generally accepted in the art as being indicative of the obesity condition. Controls for non-specific effects for these injections are done using vehicle with or without the active agent of similar composition in the same animal monitoring the same parameters or the active agent itself in animals that are thought to lack the receptor (db/db mice, fa/fa or cp/cp rats). Proteins demonstrating activity in these models will demonstrate similar activity in other mammals, particularly humans.

Since the target tissue is expected to be the hypothalamus where food intake and lipogenic state are regulated, a similar model is to inject the test article directly into the brain (e.g. i.c.v. injection via lateral or third ventricles, or directly into specific hypothalamic nuclei (e.g. arcuate, paraventricular, perifornical nuclei). The same parameters as above could be measured, or the release of neurotransmitters that are known to regulate feeding or metabolism could be monitored (e.g. NPY, galanin, norepinephrine, dopamine, β-endorphin release).

Similar studies are accomplished in vitro using isolated hypothalamic tissue in a perifusion or tissue bath system. In this situation, the release of neurotransmitters or electrophysiological changes is monitored.

The compounds are active in at least one of the above biological tests and are anti-obesity agents. As such, they are useful in treating obesity and those disorders implicated by obesity. However, the proteins are not only useful as therapeutic agents; one skilled in the art recognizes that the proteins are useful in the production of antibodies for diagnostic use and, as proteins, are useful as feed additives for animals. Furthermore, the compounds are useful for controlling weight for cosmetic purposes in mammals. A cosmetic purpose seeks to control the weight of a mammal to improve bodily appearance. The mammal is not necessarily obese. Such cosmetic use forms part of the present invention.

We claim:

1. A protein comprising the amino acids of position 95 through position 138 of SEQ ID NO: 1 properly crosslinked to SEQ ID NO: 2, or a pharmaceutically acceptable salt thereof.

2. A protein of claim 1, wherein the amino acids of positions 93 through 138 of SEQ ID NO: 1 are properly crosslinked to SEQ ID NO: 2.

3. A protein of claim 1, wherein the amino acids of positions 72 through 138 of SEQ ID NO: 1 are properly crosslinked to SEQ ID NO: 2.

4. A protein of claim 1, wherein the amino acids of positions 62 through 138 of SEQ ID NO: 1 are properly crosslinked to SEQ ID NO: 2.

5. A protein of claim 1, wherein the amino acids of positions 54 through 138 of SEQ ID NO: 1 are properly crosslinked to SEQ ID NO: 2.

6. A protein of claim 1, wherein the amino acids of positions 42 through 138 of SEQ ID NO: 1 are properly crosslinked to SEQ ID NO: 2.

7. A protein of claim 1, wherein the amino acids of positions 36 through 138 of SEQ ID NO: 1 are properly crosslinked to SEQ ID NO: 2.

8. A protein of claim 1, wherein the amino acids of positions 34 through 138 of SEQ ID NO: 1 are properly crosslinked to SEQ ID NO: 2.

9. A protein of claim 1, wherein the amino acids of positions 21 through 138 of SEQ ID NO: 1 are properly crosslinked to SEQ ID NO: 2.

10. A protein of claim 1, wherein the amino acids of positions 16 through 138 of SEQ ID NO: 1 are properly crosslinked to SEQ ID NO: 2.

11. A protein of claim 1, wherein the amino acids of positions 12 through 138 of SEQ ID NO: 1 are properly crosslinked to SEQ ID NO: 2.

12. A protein of claim 1, wherein the amino acids of positions 6 through 138 of SEQ ID NO: 1 are properly crosslinked to SEQ ID NO: 2.

13. A protein of claim 1, wherein the amino acids of positions 3 through 138 of SEQ ID NO: 1 are properly crosslinked to SEQ ID NO: 2.

14. A protein of claim 1, wherein SEQ ID NO: 1 is properly crosslinked to SEQ ID NO: 2.

15. A protein of claim 14, wherein:

Xaa at position 4 of SEQ ID NO: 1 is Gln;
Xaa at position 7 of SEQ ID NO: 1 is Gln;
Xaa at position 22 of SEQ ID NO: 1 is Asn;
Xaa at position 27 of SEQ ID NO: 1 is Thr;
Xaa at position 28 of SEQ ID NO: 1 is Gln;
Xaa at position 34 of SEQ ID NO: 1 is Gln;
Xaa at position 54 of SEQ ID NO: 1 is Met;
Xaa at position 56 of SEQ ID NO: 1 is Gln;
Xaa at position 62 of SEQ ID NO: 1 is Gln;
Xaa at position 63 of SEQ ID NO: 1 is Gln;
Xaa at position 68 of SEQ ID NO: 1 is Met;
Xaa at position 72 of SEQ ID NO: 1 is Asn;
Xaa at position 75 of SEQ ID NO: 1 is Gln;
Xaa at position 78 of SEQ ID NO: 1 is Asn;
Xaa at position 82 of SEQ ID NO: 1 is Asn;
Xaa at position 100 of SEQ ID NO: 1 is Trp;
Xaa at position 130 of SEQ ID NO: 1 is Gln;
Xaa at position 134 of SEQ ID NO: 1 is Gln;
Xaa at position 136 of SEQ ID NO: 1 is Met;
Xaa at position 138 of SEQ ID NO: 1 is Trp; and
Xaa at position 1 of SEQ ID NO: 2 is Gln.

* * * * *

UNITED STATES PATENT AND TRADEMARK OFFICE

CERTIFICATE OF CORRECTION

PATENT NO. : 5,552,524

DATED : September 3, 1996

INVENTOR(S) : Margret B. Basinski, et al

It is certified that error appears in the above-identified patent and that said Letters Patent is hereby corrected as shown below:

Column 3, line 38, reads ... "1 is Ash, Asp or Gln;" ... should read -1 is Asn, Asp or Gln;-.

Column 9, line 8, reads ... "1 is Ash, Asp or Gln;" ... should read -1 is Asn, Asp or Gln;-.

Column 12, line 11, reads ... "transformed using DBR322," ... should read -transformed using pBR322,-.

Column 13, line 8, reads ... "plasmid pCMBD (ATCC" ... should read - plasmid pCMB8 (ATCC-.

Column 14, line 67, reads ... "ATCC 7090," ... should read -ATCC 57090-.

Column 15, line 59, reads ... "NdeI to BaSHI" ... should read -NdeI to BamHI-.

Signed and Sealed this

Ninth Day of December, 1997

Attest:

Bruce Lehman

BRUCE LEHMAN

Attesting Officer

Commissioner of Patents and Trademarks